(12) United States Patent
Akmal et al.

(10) Patent No.: US 9,970,895 B2
(45) Date of Patent: May 15, 2018

(54) APPARATUS, METHOD AND SYSTEM FOR DETECTING SALT IN A HYDROCARBON FLUID

(71) Applicant: Saudi Arabian Oil Company, Dhahran (SA)

(72) Inventors: Naim Akmal, Dhahran (SA); Rashed Aleisa, Alkubar (SA); Milind Vaidya, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 36 days.

(21) Appl. No.: 15/332,555

(22) Filed: Oct. 24, 2016

(65) Prior Publication Data

US 2017/0038332 A1    Feb. 9, 2017

Related U.S. Application Data

(63) Continuation of application No. 14/982,972, filed on Dec. 29, 2015, now Pat. No. 9,513,273, which is a
(Continued)

(51) Int. Cl.
*G01N 27/413* (2006.01)
*G01N 27/26* (2006.01)
(Continued)

(52) U.S. Cl.
CPC ........... *G01N 27/413* (2013.01); *C10G 31/08* (2013.01); *G01N 27/26* (2013.01); *G01N 27/301* (2013.01);
(Continued)

(58) Field of Classification Search
None
See application file for complete search history.

(56) References Cited

U.S. PATENT DOCUMENTS 2,330,394 A    9/1943  Stuart
3,140,276 A    7/1964  Forster
(Continued)

FOREIGN PATENT DOCUMENTS

EP    1001271 A1   5/2000
GB    1125442      8/1968

OTHER PUBLICATIONS

Bjerkan et al., "Reliable Detection of Downed and Broken Conductors", 19th International Conference on Electricity Distribution, Cired, May 21-24, 2007, pp. 1-4.
(Continued)

*Primary Examiner* — Tam M Nguyen
(74) *Attorney, Agent, or Firm* — Bracewell LLP; Constance Rhebergen; Brian Tompkins (57) ABSTRACT

A method for determining a salt concentration of a hydrocarbon fluid using a conductivity sensor and a hydrocarbon testing solution includes forming the hydrocarbon testing solution. The electropolymerizable monomer is operable to form a resultant associated polymer at a peak potential of the electropolymerizable polymer. The method includes introducing the hydrocarbon testing solution into the conductivity sensor. The method includes inducing a range of potential across the hydrocarbon testing solution such that at least a portion of the electropolymerizable monomer polymerizes. The range of induced potential includes the peak potential of the electropolymerizable polymer. The method includes detecting a range of electrical current associated with the range of potential induced. The method also includes the step of determining the salt concentration of the hydrocarbon fluid using the range of potential induced and the range of electrical current detected.

18 Claims, 1 Drawing Sheet

Related U.S. Application Data continuation of application No. 13/940,900, filed on Jul. 12, 2013, now Pat. No. 9,267,909.

(60) Provisional application No. 61/671,272, filed on Jul. 13, 2012.

(51) Int. Cl.
*C10G 31/08* (2006.01)
*G01N 33/28* (2006.01)
*G01N 27/416* (2006.01)
*G01N 27/30* (2006.01)

(52) U.S. Cl.
CPC ..... *G01N 27/4163* (2013.01); *G01N 27/4166* (2013.01); *G01N 33/2835* (2013.01)

(56) References Cited

U.S. PATENT DOCUMENTS

| | | | |
|---|---|---|---|
| 3,181,058 | A | 4/1965 | Gulbrandsen |
| 4,684,457 | A | 8/1987 | McKechnie et al. |
| 4,851,782 | A | 7/1989 | Jeerings et al. |
| 5,489,371 | A | 2/1996 | Joseph et al. |
| 5,746,908 | A | 5/1998 | Mitchell |
| 5,839,093 | A | 11/1998 | Novosel et al. |
| 6,268,737 | B1 | 7/2001 | Marszalek |
| 6,278,282 | B1 | 8/2001 | Marszalek |
| 6,718,271 | B1 | 4/2004 | Tobin |
| 8,027,364 | B2 | 9/2011 | Becattini et al. |
| 8,077,049 | B2 | 12/2011 | Yaney et al. |
| 2005/0040809 | A1 | 2/2005 | Uber, III et al. |
| 2008/0097706 | A1 | 4/2008 | McCormack et al. |
| 2009/0281679 | A1 | 11/2009 | Taft et al. |
| 2009/0289637 | A1 | 11/2009 | Radtke |
| 2010/0007354 | A1 | 1/2010 | Deaver, Sr. et al. |
| 2011/0074436 | A1 | 3/2011 | Nowicki et al. |

OTHER PUBLICATIONS

Bjerkan, "Efficient Fault Management using Remote Fault Indicators", Cired, Jun. 8-11, 2009, pp. 1-25.
International Search Report and Written Opinion for Related PCT Application PCT/US2013/050276 (SA5061/PCT), dated Sep. 24, 2013.
Fortuny et al: "Measuring Salinity in crude oils: Evaluation of methods and an improved procedure", Fuel, IPC Science and Technology Press, Guildford, GB, vol. 87, No. 7; Feb. 22, 2008, pp. 1241-1248, XP022495860, ISSN: 0016-2361, DOI: 10.1016/J.F.
Garcia-Santander et al., "Down-conductor fault detection and location via a voltage based method for radial distribution networks", IEE Proc., Mar. 2005, pp. 180-184, vol. 152, No. 2, IEE.
PCT International Search Report and the Written Opinion of the International Searching Authority dated Dec. 18, 2013; International Application No. PCT/US2013/059673 (SA5094/PCT); International File Date: Sep. 13, 2013.
Schneider Electric, "Medium Voltage Distribution Easergy Range Fault detection and remote control", Brochure, pp. 1-2.
Schneider, "Wireless Communicating Indicator FLITE116—G200—DNP3 User's Manual". pp. 1-61.
Vekara et al., "Remote Monitoring System for Transformer Substations", pp. 1-3.

APPARATUS, METHOD AND SYSTEM FOR DETECTING SALT IN A HYDROCARBON FLUID

CROSS-REFERENCE TO RELATED PATENT APPLICATIONS

This application is a continuation of and claims priority to U.S. patent application Ser. No. 14/982,972 titled "Apparatus, Method, and System for Detecting Salt in a Hydrocarbon Fluid" and filed on Dec. 29, 2015, now U.S. Pat. No. 9,513,273, which is a continuation of and claims priority to U.S. patent application Ser. No. 13/940,900 titled "Apparatus, Method, and System for Detecting Salt in a Hydrocarbon Fluid" and filed on Jul. 12, 2013, now U.S. Pat. No. 9,267,909, which claims priority to U.S. Provisional Application No. 61/671,272, filed Jul. 13, 2012, each of which is incorporated by reference in its entirety for the purposes of United States patent practice

BACKGROUND OF THE INVENTION

1. Field of the Invention

The field of invention relates to processing hydrocarbon fluids. More specifically, the field relates to an apparatus, method and system for monitoring salts in a hydrocarbon fluid.

2. Description of the Related Art

The amount of salt in a hydrocarbon fluid is a significant factor in several types of transport and refining process problems. Fouling, deactivation of catalyst and severe corrosion are indications of long-term exposure to salt in a feed. The type and amount of salt in the hydrocarbon fluid depends mostly on the source, which in turn can reflect the severity in which hydrocarbons are being drawn from the source or the overall age of the source field. In addition, residual salt water from shipment tankers or handling mishaps can also contaminate the hydrocarbon fluid to a point where the consumer cannot effectively process it. The presence of salt in the hydrocarbon fluid, even as low as in the parts per million (ppm) range, can cause significant damage to refining and chemical processing equipment over a short period.

Dispersed, small water droplets in the hydrocarbon fluid dissolve and retain the salt. The chemical composition of the salt can vary; however, typically the salt found in produced hydrocarbon fluid is sodium chloride with lesser amounts of calcium and magnesium chlorides.

The determination of the salt concentration in the hydrocarbon fluid, especially hydrocarbon fluids made of a crude oil or a natural gas condensate, takes significant amount of effort using current methods. Current testing techniques cannot reliability or with the necessary sensitivity (sub-ppm) determine salt concentration in a timely manner. Laboratory testing and offline measurements are the only reliable means for accurately determining salt concentration in the hydrocarbon fluid to this level. American Standard Test Methods (ASTM) D 3230 & D 6470 are the standardized laboratory tests for measuring the salt concentration in a crude oil. ASTM D 3230 is an electrometric method that requires extensive sample preparation with numerous solvents, including xylene, 1 butanol and methyl alcohol. ASTM D 6470, a potentiometric technique, requires extensive sample preparation as well as additional equipment and labor. Besides being off-line and not expedient, the other procedural and equipment requirements for both of these methods limit their application towards online or "real time" salt concentration determination. As with any testing method, the "human element" can also inadvertently influence the results and add a layer of variability.

Current online salinity sensors depend on directly testing non-conductive paraffinic materials in an attempt to detect the presence of an electroactive specie (that is, salt) in the bulk fluid. Existing sensors use conductive electrodes inserted into flowing crude oil. The salinity sensors apply potential directly into the hydrocarbon fluid in an attempt to determine conductivity of the bulk fluid. This technique sacrifices the testing apparatus by having anodic and cathodic ions directly attack the elements of the apparatus. Corrosion on the sensor probes occurs due to conductive-metal reduction-oxidation reactions on both the working and counter electrodes when water is present. The salts also precipitate directly onto the surface of the probes. Salt on the surface of the probes causes physical deterioration through galvanic pitting even during periods of non-use. Modification to the probe surface area also changes the meaning of surface-area sensitive responses, for example, surface current density or voltage per unit area. The technique is also not accurate because of the general non-conductivity of the bulk hydrocarbon fluid. The presence of heavy paraffin materials can also cause variations in salinity values. As for the method of testing, conductivity can change when a shift in temperature occurs, leading to varying salinity values for the same hydrocarbon fluid sample.

Measuring the salt content in hydrocarbon fluid down to the sub-ppm level before introducing the material to transportation, refining or a desalting process is desirable. Currently, there are no useful techniques to determine salt concentration to the ppm level considered both expeditious and reliable enough to meet commercial transportation and refining needs. A testing apparatus, method and system that makes it possible for expedient salinity determination is desirable. The apparatus and system should be reliable and resilient in the hydrocarbon fluid, especially in use with a salinity treatment system.

SUMMARY OF THE INVENTION

A hydrocarbon testing solution is useful for determine the salt concentration in a hydrocarbon fluid includes the hydrocarbon fluid that contains the salt, an electropolymerizable monomer and a non-aqueous solvent. The hydrocarbon fluid includes the salt and a hydrocarbon selected from a group consisting essentially of a crude oil, a natural gas condensate, a crude oil fraction, a post-petrochemical processed material and combinations thereof. The electropolymerizable monomer is operable in the hydrocarbon testing solution to form a resultant associated polymer at a peak potential of the electropolymerizable polymer.

A conductivity sensor useful for determining the salt concentration of the hydrocarbon testing solution by forming a resultant associated polymer includes a housing that is operable to contain the hydrocarbon testing solution and is non-conductive. The conductivity sensor includes a three-electrode set that is positioned within the housing and includes a working electrode, a counter electrode and a reference electrode. The working electrode has a first surface area and the counter electrode has a second surface area. The second surface area is greater than the first surface area. The working and reference electrodes together are operable to induce a potential in the hydrocarbon testing solution. The working and counter electrodes together are operable to detect a current in the hydrocarbon testing solution. The conductivity sensor includes a mixing apparatus positioned within the housing.

A method for determining a salt concentration of a hydrocarbon fluid using a conductivity sensor and a hydrocarbon testing solution includes the step of forming the hydrocarbon testing solution as previously described. The method also includes the step of introducing the hydrocarbon testing solution into the conductivity sensor as previously described. The method also includes the step of inducing a range of potential across the hydrocarbon testing solution contained in the conductivity sensor such that at least a portion of the electropolymerizable monomer in the hydrocarbon testing solution polymerizes into the resultant associated polymer and such that the hydrocarbon testing solution forms an exhausted hydrocarbon testing solution. The range of induced potential includes the peak potential of the electropolymerizable polymer. The method also includes the step of detecting a range of electrical current associated with the range of potential induced using the conductivity sensor. The range of detected electrical current includes the peak current. The method also includes the step of determining the salt concentration of the hydrocarbon fluid using the range of potential induced across the hydrocarbon testing solution and the range of electrical current detected by the conductivity sensor.

A method of treating a hydrocarbon fluid includes the step of forming a hydrocarbon testing solution. The hydrocarbon testing solution includes the hydrocarbon fluid to be treated, an electropolymerizable monomer and a non-aqueous solvent. The hydrocarbon fluid includes a salt. The electropolymerizable monomer is operable in the hydrocarbon testing solution to form a resultant associated polymer at the peak potential of the electropolymerizable polymer. The method includes the step of introducing the hydrocarbon testing solution into a conductivity sensor. The conductivity sensor includes a working electrode, a counter electrode and a reference electrode. The method includes the step of inducing a range of potential across the hydrocarbon testing solution contained in the conductivity sensor. The induction is such that at least a portion of the electropolymerizable monomer in the hydrocarbon testing solution polymerizes into the resultant associated polymer. The induction also is such that the hydrocarbon testing solution forms an exhausted hydrocarbon testing solution. The range of induced potential includes the peak potential of the electropolymerizable polymer. The method includes the step of detecting a range of electrical current associated with the range of potential induced using the conductivity sensor. The range of detected electrical current includes the peak current. The method includes the step of determining the salt concentration of the hydrocarbon fluid using the range of potential induced across the hydrocarbon testing solution and the range of electrical current detected by the conductivity sensor. The method includes the step of determining the amount of hydrocarbon fluid to be treated. The method includes the step of introducing an amount of salt-extracting fluid into the hydrocarbon fluid. The introduction is such that a salt-bearing salt-extracting fluid and a desalinated hydrocarbon fluid form. The amount of salt-extracting fluid introduced is based upon the determined salt concentration of the hydrocarbon fluid and the determined amount of hydrocarbon fluid to be treated. The method includes the step of separating the salt-bearing salt-extracting fluid from the desalinated hydrocarbon fluid.

The conductivity sensor that is operable to induce electropolymerization of the electropolymerizable monomer mixed with the hydrocarbon fluid containing the salt provides the peak current value at the peak polymerization potential for the electropolymerizable monomer. The salt concentration determination system supplies the hydrocarbon testing solution, which contains the hydrocarbon fluid and the electropolymerizable monomer. Identifying the peak current using the hydrocarbon testing solution allows for the determination of peak current height, which is a function of the amount of salt present in the hydrocarbon testing solution. The peak current height directly correlates with the concentration of the salt in the hydrocarbon fluid.

Polymerization of the electropolymerizable monomer does not cause physical or chemical degradation to the conductivity sensor. In fact, in some instances the polymer protects the electrodes of the conductivity sensor from salt and ion-based degradation. Polymerization does not occur without the presence of an electroactive species that facilitates electron transfer through the hydrocarbon fluid. The hydrocarbon fluid provides the electroactive species: salt.

The intensity of the peak current, otherwise known as "peak current height", is proportional to the concentration of salt in the hydrocarbon testing solution. The relationship between the peak current height and the salt concentration is a function of the proportional amounts of hydrocarbon fluid, the non-aqueous solvent and the electropolymerizable monomer in the hydrocarbon testing solution; the types of non-aqueous solvent and electropolymerizable monomer; and the amount of salt in the hydrocarbon fluid. Given steady state conditions and concentrations otherwise between hydrocarbon testing solution samples, a greater peak current height results from a greater amount of salt present. The relationship between detected peak current height and salt concentration in the hydrocarbon fluid is directly proportional.

The conductivity sensor of the invention advantageously does not require adjustment for process conditions, including temperature. The basis for the peak current detected by the conductivity sensor is the concentration of components—that is, monomer, salt, solvent—and not other process conditions. The conductivity sensor achieves detection of sub-ppm concentration of electrically active and ionic species, including salts.

In the conductivity sensor, electrons pass through the hydrocarbon testing solution along the electropolymerizable monomer molecules and the salts dissolved in the hydrocarbon testing solution. Radicalized monomer molecules form oligomers and polymeric chains. Although not intending to be bound by theory, it is believed that the resultant associated polymer forms at the electrodes and as fine strands between (but not necessarily connecting) the working and counter electrodes of the conductivity sensor. The polymerization reaction is nearly instantaneous at the peak potential.

The conductivity sensor and the salt concentration determination system avoid the deleterious effects of directly applying voltages to the hydrocarbon fluids containing the salt as previously described, including salt-induced corrosion of the electrodes. Because of the near-instantaneously conversion of the electropolymerizable monomer into its resultant associated polymer, the apparatus and system provide fast, reliable and reproducible data by applying the potential in a known and narrow voltage range.

Lengthy sample preparation and a number of solvents as required using ASTM and other laboratory techniques are unnecessary. Rather, the embodiment method of using the embodiment conductivity sensor can result in periodic and even continuous conductivity detection with proper selection and design of the non-aqueous solvent and the electropolymerizable monomer delivery system.

With reliable determination of the peak current height, determination of salt concentration values in the hydrocarbon fluid is reliable and expedient. Operators and control systems alike can use the determined salt concentration to introduce the salt-extracting fluid into the hydrocarbon fluid as part of the salt extraction process.

BRIEF DESCRIPTION OF THE DRAWINGS

These and other features, aspects, and advantages of the present invention are better understood with regard to the following Detailed Description of the Preferred Embodiments, appended Claims, and accompanying FIGURES, where:

DETAILED DESCRIPTION OF THE PREFERRED EMBODIMENTS

The Specification, which includes the Summary of Invention, Brief Description of the Drawings and the Detailed Description of the Preferred Embodiments, and the appended Claims refer to particular features (including process or method steps) of the invention. Those of skill in the art understand that the invention includes all possible combinations and uses of particular features described in the Specification. Those of skill in the art understand that the invention is not limited to or by the description of embodiments given in the Specification. The inventive subject matter is not restricted except only in the spirit of the Specification and appended Claims.

Those of skill in the art also understand that the terminology used for describing particular embodiments does not limit the scope or breadth of the invention. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a", "an" and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur. "Operable" and its various forms means fit for its proper functioning and able to be used for its intended use. "Associated" and its various forms means something connected with something else because they occur together or that one produces the other.

Spatial terms describe the relative position of an object or a group of objects relative to another object or group of objects. The spatial relationships apply along vertical and horizontal axes. Orientation and relational words including "upstream" and "downstream"

Where the Specification or the appended Claims provide a range of values, it is understood that the interval encompasses each intervening value between the upper limit and the lower limit as well as the upper limit and the lower limit. The invention encompasses and bounds smaller ranges of the interval subject to any specific exclusion provided.

Where the Specification and appended Claims reference a method comprising two or more defined steps, the defined steps can be carried out in any order or simultaneously except where the context excludes that possibility.

FIG. 1

Figure 1:
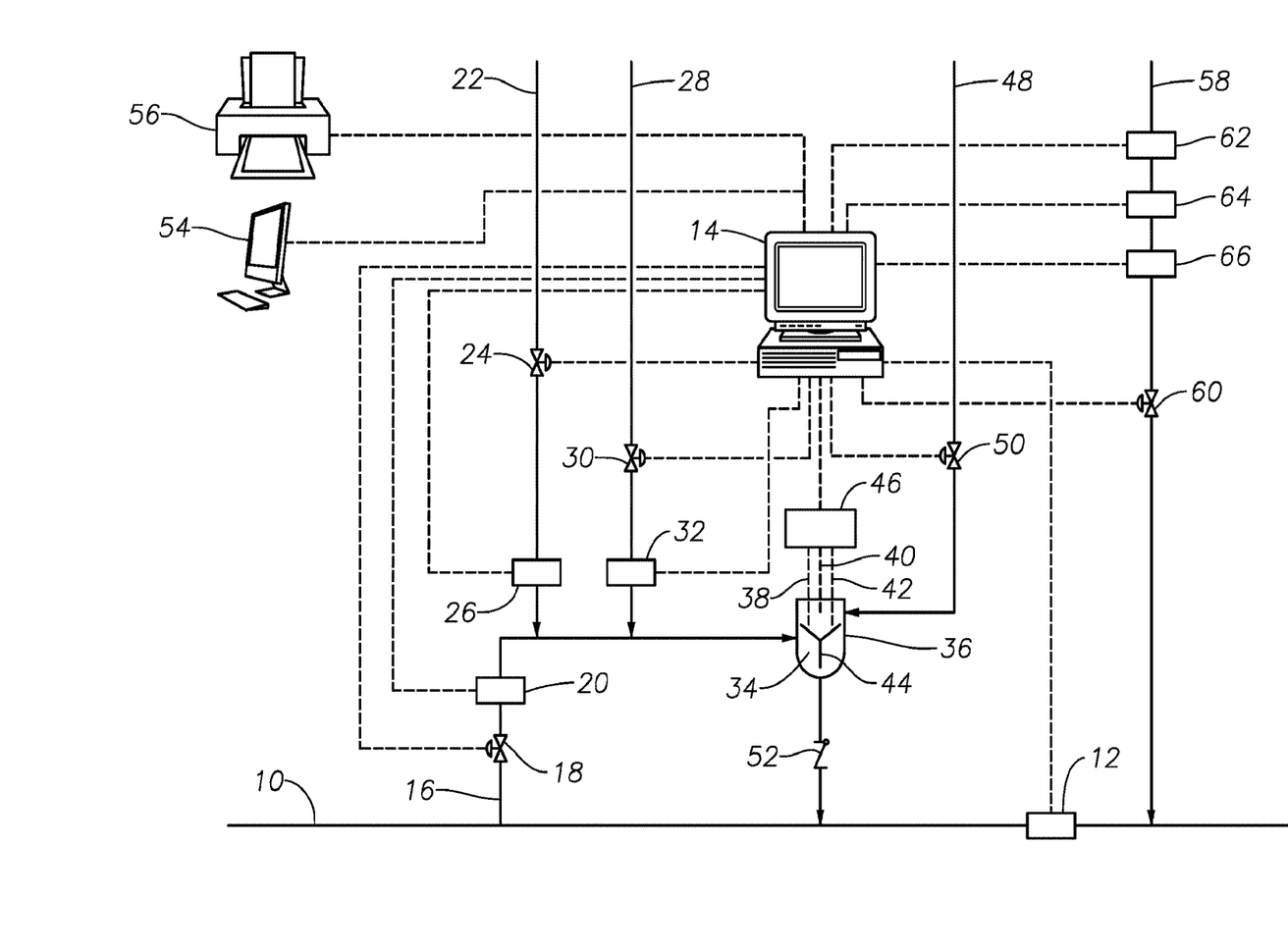
FIG. 1 is a general flow and control schematic of a system using an embodiment of the conductivity sensor for performing the steps of an embodiment of the method of determining a salt concentration of a hydrocarbon fluid and for treating a hydrocarbon fluid containing salt.

FIG. 1 is a general flow and control schematic of a system using an embodiment of the conductivity sensor for performing the steps of an embodiment of the method of determining a salt concentration of a hydrocarbon fluid and for treating a hydrocarbon fluid containing salt. FIG. 1 and its description facilitate a better understanding of the conductivity sensor, the hydrocarbon testing solution and methods of their use. In no way should FIG. 1 limit or define the scope of the invention. FIG. 1 is a simple diagram for ease of description. Those of ordinary skill in the art understand that such systems are complex structures with ancillary equipment and subsystems that render them operable for their intended purpose.

FIG. 1 shows hydrocarbon fluid supply line 10, which conveys hydrocarbon fluid containing salt from upstream facilities and sources, including storage tank, pipeline and wellheads (not shown) to downstream facilities, including storage tanks, pipelines and processing units (not shown). Hydrocarbon fluid flow sensor 12 provides a signal in response to the detected rate of fluid flow through hydrocarbon fluid supply line 10. Hydrocarbon fluid flow sensor 12 is in signal communication with computer controller 14.

Sampling line 16 couples to hydrocarbon fluid supply line 10 and diverts a portion of the hydrocarbon fluid to conductivity testing. The amount of the hydrocarbon fluid diverted for conductivity testing is dependent on the position of sampling line fluid control valve 18. Sampling line fluid control valve 18 is in signal communication with computer controller 14. Sampling line flow sensor 20 provides a signal in response to the detected rate of fluid flow through sampling line 16. Sampling line flow sensor 20 is in signal communication with computer controller 14.

Solvent injection line 22 couples to sampling line 16 and introduces the non-aqueous solvent into sampling line 16 such that it intimately mixes with the hydrocarbon fluid in sampling line 16. The amount of non-aqueous solvent introduced is dependent on the position of solvent injection line flow control valve 24. Solvent injection line flow control valve 24 is in signal communication with computer controller 14. Solvent injection line flow sensor 26 provides a signal in response to the detected rate of non-aqueous solvent flow into sampling line 16. Solvent injection line flow sensor 26 is in signal communication with computer controller 14.

Monomer injection line 28 couples to sampling line 16 and introduces the electropolymerizable monomer into sampling line 16 such that it intimately mixes with the mixture of the hydrocarbon fluid and the non-aqueous solvent in sampling line 16 before being introduced into conductivity sensor (dotted box 34). Mixing the hydrocarbon fluid, the non-aqueous solvent and the electropolymerizable monomer forms the hydrocarbon testing fluid. The amount of electropolymerizable monomer introduced is dependent on the position of monomer injection line flow control valve 30. Monomer injection line flow control valve 30 is in signal communication with computer controller 14. Monomer injection line flow sensor 32 is provides a signal in response to the detected rate of electropolymerizable monomer flow into sampling line 16. Monomer injection line flow sensor 32 is in signal communication with computer controller 14.

Sampling line 16 couples to conductivity sensor 34 and introduces the hydrocarbon testing solution to the interior of conductivity sensor 34 for conductivity testing. FIG. 1 shows conductivity sensor 34 having shell 36 through which the three electrodes—working 38, counter 40 and reference 42—pass. Conductivity sensor 34 also houses mixing apparatus 44, which stirs the contents of conductivity sensor 34.

Working electrode 38, counter electrode 40 and reference electrode 42 couple to and are in both electrical and signal communications with potentiostat-galvanostat 46. Potentiostat-galvanostat 46 provides a sweeping potential to the hydrocarbon testing solution between working 38 and reference 42 electrodes. Potentiostat-galvanostat 46, through conductivity sensor 34, detects the current conducted by the hydrocarbon testing solution between working 38 and counter 40 electrodes while the potential sweeps between a first potential value and a second potential value. Potentiostat-galvanostat 46 is in signal communication with computer controller 14.

Polymer solvent line 48 couples to conductivity sensor 34 and introduces a solvent into conductivity sensor 34 that removes any resultant polymer that forms in conductivity sensor 34. Polymer associated with the electropolymerizable monomer can form on working electrode 38 as a result of performing the detection method. The flow rate and timing of the introduction of polymer solvent is dependent on the position of polymer solvent flow control valve 50. Polymer solvent flow control valve 50 is in signal communication with computer controller 14.

Sampling return line 52 couples to conductivity sensor 34 and conveys exhausted hydrocarbon testing solution from conductivity sensor 34 into hydrocarbon fluid supply line 10 downstream of the location where sampling line 16 couples to hydrocarbon fluid supply line 10. Exhausted hydrocarbon testing solution forms during conductivity testing from the introduced hydrocarbon testing solution.

Computer controller 14 is in signal communication with output devices, including display monitor 54 and printer 56. Computer controller 14 provides computer-processed information of conductivity testing, sensor information and process flow values for human interpretation using pre-programmed computer instructions.

FIG. 1 also shows steam injection line 58 coupling to hydrocarbon fluid supply line 10 downstream of hydrocarbon fluid flow sensor 12. Steam injection line 58 introduces steam into hydrocarbon fluid supply line 10 such that steam intimately mixes with the hydrocarbon fluid in hydrocarbon fluid supply line 10. The amount of steam introduced into hydrocarbon fluid supply line 10 is dependent on the position of steam flow control valve 60. Steam flow control valve 60 is in signal communication with computer controller 14. Steam flow sensor 62, steam pressure sensor 64 and steam temperature sensor 66 provide signals in response to the flow rate, the pressure and the temperature of the steam, respectively, for hydrocarbon fluid supply line 10. Steam flow sensor 62, steam pressure sensor 64 and steam temperature sensor 66 are each in separate signal communication with computer controller 14.

Computer controller 14 has a set of computer-readable instructions (that is, a program) and data stored in a combination of physical and virtual computer-accessible memory that permits the execution of steps for determining salt concentration in the hydrocarbon fluid using the salt concentration determination system. Data stored in the computer-accessible memory includes machine-readable information related to the formula or ratio of hydrocarbon testing solution components. Computer controller 14 accesses computer-accessible memory when determined by the computer-readable instructions.

Computer controller 14 transmits signals to external devices, including flow control valves, to regulate elements of the salt concentration determination system and formulate the hydrocarbon testing solution. For example, computer controller 14 transmits a signal to mixing apparatus 44 of conductivity sensor 34 to provide continuous stirring of the hydrocarbon testing solution contained in shell 36. Computer controller 14 uses a set of computer-readable instruction, including subroutines that include instructions for using well-known and understood statistical, mathematical and relationship algorithms, and accesses historical and current data stored in computer-accessible memory, including current valve positions and detected flow rates, to periodically or continually maintain, adjust and modifies aspects of the salt concentration determination system according to the desired formulation of the hydrocarbon testing solution for salt concentration determination.

Computer controller 14 transmits an appropriate open control valve position signal to sampling line fluid control valve 18 to introduce an amount of the hydrocarbon fluid into conductivity sensor 34. Sampling line flow sensor 20 detects the flow and provides a flow signal in response to computer controller 14. Computer controller 14 periodically adjusts the position of sampling line fluid control valve 18 via transmission of control valve position signal based upon the flow signal response from sampling line flow sensor 20 to ensure introduction of the appropriate proportional amount of hydrocarbon fluid to conductivity sensor 34.

Computer controller 14 also transmits an appropriate open control valve position signal to solvent injection line flow control valve 24 to introduce an amount of non-aqueous solvent into conductivity sensor 34. Solvent injection line flow sensor 26 detects the flow and provides to computer controller 14. Computer controller 14 periodically adjusts the position of solvent injection line flow control valve 24 via transmission of control valve position signal based upon the flow signal response from solvent injection line flow sensor 26 to ensure introduction of the appropriate proportional amount of non-aqueous solvent to conductivity sensor 34.

Computer controller 14 also transmits an appropriate open control valve position signal to monomer injection line flow control valve 30 to introduce an amount of electropolymerizable monomer into conductivity sensor 34. Monomer injection line flow sensor 32 detects the flow and provides to computer controller 14. Computer controller 14 periodically adjusts the position of monomer injection line flow control valve 30 via transmission of control valve position signal based upon the flow signal response from monomer injection line flow sensor 32 to ensure introduction of the appropriate proportional amount of electropolymerizable monomer to conductivity sensor 34.

The hydrocarbon testing solution forms in sampling line 16 upon introduction of all three components. Hydrocarbon testing solution passes into the interior of conductivity sensor 34 for testing.

Computer controller 14 transmits a signal to potentiostat-galvanostat 46 to induce a sweeping potential of the hydrocarbon testing solution in conductivity sensor 34. Potentiostat-galvanostat 46 induces a sweeping potential in the hydrocarbon testing solution between a first pre-set potential value and a pre-set second potential value using working electrode 38 and reference electrode 42. Potentiostat-galvanostat 46 applies the sweeping potential at a steady sweep rate to the hydrocarbon testing solution.

Conductivity sensor 34, in response, detects the resultant electrical current produced from the inducement of potential between working electrode 38 and counter electrode 40. For the range of applied potential, including the peak polymerization potential for the electropolymerizable monomer in the hydrocarbon testing solution, conductivity sensor 34 detects the associated electrical current at the applied potentials, including the peak electrical current.

Potentiostat-galvanostat 46 correlates the values of the potential applied to conductivity sensor 34 with the detected electrical current values from conductivity sensor 34 and transmits the potential-current data to computer controller 14 upon completion of the potential sweep.

Computer controller 14 uses a set of computer-readable instruction and is operable to access historical and current data stored in computer-accessible memory, including the correlated potential-current data from potentiostat-galvanostat 46 and data from sensors including hydrocarbon fluid flow rate from hydrocarbon fluid flow sensor 12, to determine the peak current value, the peak current height, the concentration of salt in the hydrocarbon testing solution and the concentration of salt in the hydrocarbon fluid.

Computer controller 14 communicates with display monitor 54 and printer 56 and provides determined information in formats suitable for human interpretation, including graphically, numerically, schematically and textually.

Computer controller 14 also has a set of computer-readable instruction (that is, program) and data stored in a combination of physical and virtual computer-accessible memory that permits the execution of steps for the salt extraction process. The determined salt concentration is useful for determining the amount of salt in the hydrocarbon fluid flowing through hydrocarbon fluid supply line 10. In turn, the amount of salt in the hydrocarbon fluid dictates the amount of salt-extraction fluid for treating the hydrocarbon fluid. Data stored in computer-accessible memory includes machine-readable information related to ratios of salt-extraction fluid to salt concentration or amounts and hydrocarbon fluid flow. Computer controller 14 accesses computer-accessible memory when determined by computer-readable instruction.

Computer controller 14 uses a set of computer-readable instruction and accesses historical and current data stored in computer-accessible memory, including the determined salt concentration, the flow signal from hydrocarbon fluid flow sensor 12, the flow signal from steam flow sensor 62, the pressure signal from steam pressure sensor 64 and the temperature signal from steam temperature sensor 66 of the steam in steam injection line 58, to determine the amount of steam to introduce to the hydrocarbon fluid in hydrocarbon fluid supply line 10 for downstream salt extraction.

Computer controller 14 transmits an appropriate open control valve position signal to steam flow control valve 60 to introduce an amount of steam into hydrocarbon fluid in hydrocarbon fluid supply line 10 for downstream salt extraction treatment. Computer controller 14 periodically adjusts the position of steam flow control valve 60 via transmission of control valve position signal based upon changes to any of the prior referenced sensor signal readings and determined values, especially the determined salt concentration value, to ensure introduction of the appropriate amount of steam into the hydrocarbon fluid for the amount of salt it contains.

Periodically, computer controller 14 introduces an amount of polymer solvent into conductivity sensor 34 through polymer solvent line 48 by transmitting an appropriate signal to polymer solvent flow control valve 50 to open. The amount introduced is sufficient to remove any resultant associated polymer from conductivity sensor 34.

Hydrocarbon Testing Solution

The hydrocarbon testing solution useful for determining salt content in the hydrocarbon fluid includes proportional amounts of the hydrocarbon fluid, the electropolymerizable monomer and the non-aqueous solvent. The hydrocarbon fluid has salt, which functions as the electroactive constituent of the hydrocarbon testing solution. The electropolymerizable monomer and the non-aqueous solvent do not provide electroactive agents. The salt facilitates the electrochemical polymerization reaction that produces the electrical current.

Hydrocarbon Fluid

The hydrocarbon fluid includes unfractionated and undistilled crude oils, natural gas condensates, crude oil fractions, post-petrochemical processed materials and combinations thereof. The term "hydrocarbon" includes other materials besides those bearing only hydrogen and carbon atoms. Those skilled in the art understand that untreated and undistilled hydrocarbon fluids often contain compounds that include oxygen, sulfur and nitrogen; organometallic compounds; and metal ions, including vanadium, copper and nickel in organic-metal complexes. Hydrocarbons that are liquids at atmospheric pressure and temperatures typically contain organic sulfur, nitrogen and oxygen compounds, including alkane and cycloalkane sulfides, mercaptans, disulfides, polysulfides and thiophenes. Hydrocarbon fluid can contain up to several percent by weight heterorganic compounds.

As previously stated, hydrocarbon fluid also includes previously processed, distilled or fractionated hydrocarbons, which includes atmospheric pressure boiling point crude oil fractions. Examples of such fractions include naphtha, kerosene and diesel gas oil. In some instances, the hydrocarbon fluid can also include vacuum-based distillates, paraffin oils and fractions containing some amount of asphaltenes and maltenes. In an embodiment of the hydrocarbon testing solution the hydrocarbon fluid includes a post-petrochemical processed material contaminated with seawater. Seawater contamination of expensive, highly refined hydrocarbon fluids that are post-processed materials can motivate application of the desalination method to make the material suitable for processing once again.

Salt in Hydrocarbon Fluid

The hydrocarbon fluid before desalination includes a concentration of salt. The salt concentration of produced crude oil is typically in a range of from about 20 to about 2000 milligrams (mg) per kilogram of crude oil. Seawater contaminated materials can have significantly greater levels of salt. Seawater contains approximately 35 grams of salts per kilogram of seawater. An embodiment of the hydrocarbon testing solution has a salt concentration in a range of from about 20 mg to about 35 g of salt per kilogram of hydrocarbon fluid.

The dominant salt in hydrocarbon fluid is sodium chloride, but it is not the only salt. Salts of several alkali, alkaline earth and transition metals coupled with halide, nitrate, sulfate and carbonate counter-ions are potentially present. Example of salts include magnesium chloride, sulfate, and bromide; calcium chloride, bromide, and sulfate; sodium chloride and sulfate; zinc bromide; and potassium chloride and iodide.

Electropolymerizable Monomer

The hydrocarbon testing solution includes the electropolymerizable monomer. An embodiment of the hydrocarbon testing solution includes where the volume percentage ratio of the amounts of the electropolymerizable monomer to the hydrocarbon fluid is in a range of from about 0.01 to about 10000.

Electrochemical polymerization of the monomer in the hydrocarbon testing solution occurs upon application of a particular "peak" potential between the working and counter electrodes in the conductivity sensor. Each electropolymerizable monomer has a narrow or limited potential range where, upon application, electropolymerization occurs. The resultant associated polymer forms upon polymerization. The potential range or value where the monomer/polymer conversion occurs is dependent on the monomer. Process conditions, including temperature, and other hydrocarbon testing solution constituents do not influence the "peak" potential of the electropolymerizable monomer.

Although not intending to be bound by theory, it is believed that upon application of the "peak" potential in the presence of the monomer, electrons transfer from the charge-inducing apparatus (for example, electrodes) to the monomer molecules proximate to the apparatus. In an electrochemical cell, the monomer molecules proximate to the counter electrode receive electrons and electrons are removed from the monomer proximate to the working electrode. The generation of anions and cations of unsaturated monomers initiates the electropolymerization of the monomer molecules. The polymerization reaction can occur through a variety of known polymerization reaction mechanism depending on the monomer type, including anionic and cationic chain addition, free radical addition and electrochemical oxidation. The reaction is near instantaneous and only the availability of monomer limits the reaction.

The reaction of radicalized monomers produces a detectable electrical current that has a maximum or apex value ("peak current") at the "peak potential". Monomers reacting with one another and forming associated polymers around and between the electrodes transfer electrons freely, producing the detectable current via free electron transfer. Higher induced voltage from the "peak potential" usually reveals current attenuation from the peak current value due to reduced concentrations of electropolymerizable monomer proximate to and in between the working and counter electrodes.

Useful examples of electropolymerizable monomers for the hydrocarbon testing solution include acetylene; acrylonitriles, including methyl acrylonitrile; anilines, including derivatives bearing sulpho, carboxyl and hydroxyl functional groups; azulene; mono-carbazoles, including vinyl carbazole, N-carbazole and monoethyl-carbazole; dicarbazoles, including 2,6-bis-carbazol-9-yl-hexanoic acid pentafluorophenyl ester, 2,6-bis-carbazol-9-yl-hexanoic acid 2,5-dioxo-pyrrolidin-1-yl ester, 2,6-bis-carbazol-9-yl-hexanoic acid 1,3-dioxo-1,3-dihydro-isoindol-2-yl ester, 2,6-bis-carbazol-9-yl-hexanoic acid methyl ester, 2,6-bis-carbazol-9-yl-hexanoic acid, 2,6-bis-carbazol-9-yl-hexan-1-ol acetate, 2,6-bis-carbazol-9-yl-chlorohexane and 2,6-bis-carbazol-9-yl-hexan-1-ol; tetrathiafulvalene; naphthalenes, including diaminonaphthalene; indole; pyrroles, including N-substituted pyrroles, N-functionalized pyrroles, N-methyl-N'-(6-pyrrol-1-ylhexyl)-4,4'-bipyridinium dihexafluorophosphate and N,N'-bis(6-pyrrol-1-ylhexyl)-4,4'-bipyridinium dihexafluorophosphate; thiophenes, including 2,2'-bithiophene, 3-methyl thiophene, 3-bromothiophene, 3,4-dibromo thiophene, 3,4-dimethylthiophene, 3,4-methyl ethyl thiophene, 3,4-diethyl thiophene, 3-thiomethyl thiophene, benzo-thiophene and dibenzo-thiophene; phenyl quinolone; phenylenes, including para-phenylene, para-phenylene vinylene and phenylene sulfide; pyridine; acrylates, including methyl methacrylate and ethyl acrylate; styrene; and vinylmetallo monomers, which are vinyl monomers with organometallic side units that form polyvinyl metallo polymers upon electropolymerization. An embodiment of the hydrocarbon testing solution includes an electropolymerizable monomer that is selected from the group consisting essentially of anilines; acetylene; pyrroles; thiophenes, including benzo-thiophene and dibenzothiophene; indoles, azines, para-phenylenevinylenes, para-phenylenes, pyrenes, furans, selenophenes, pyrridazines, carbazoles, (methyl) acrylates and pyridine, and their derivatives, crown ethers and combinations thereof. An embodiment of the hydrocarbon testing solution includes an electropolymerizable monomer that is selected from the group consisting essentially of thiophene, thiophene-derivatives, aniline, aniline-derivatives, crown ethers and combinations thereof. One of ordinary skill in the art understands that suitable electropolymerizable monomers also include all derivatives of the monomer species identified as well as other electropolymerizable monomers not identified but suitable for electrochemical polymerization processes in hydrocarbon-based solutions.

An embodiment of the hydrocarbon testing solution includes where the electropolymerizable monomer is operable to form a resultant associated polymer that is electrically conductive.

Non-Aqueous Solvent

The hydrocarbon testing solution includes an amount of the non-aqueous solvent. The solvent facilitates ion transfer during application of potential between the electrodes. The non-aqueous solvent also helps disperse salt from the hydrocarbon fluid for use during electropolymerization. An embodiment of the hydrocarbon testing solution includes where the volume percentage ratio of the amounts of non-aqueous solvent to hydrocarbon fluid is in a range of from about 0.01 to about 10000, and preferably in a range of from about 9 to about 99.

A useful non-aqueous solvent does not hinder or prevent the electrochemical polymerization reaction from occurring. For example, those of ordinary skill in the art understand that certain solvents are not appropriate for use with the monomer thiophene and its derivatives because the solvent has a dielectric constant lower than thiopene. Examples of solvents with lower-than-thiopene dielectric constant include water, chlorobenzene and anisole.

The non-aqueous solvent does not have to be a solvent of the electropolymerizable monomer, but the non-aqueous solvent selected should not hinder the solubility of the monomer in the hydrocarbon testing solution.

An embodiment of the hydrocarbon testing solution includes the non-aqueous solvent that is a solvent for the resultant associated polymer formed from the polymerization of the electropolymerizable monomer. Such an embodiment can prevent formation of polymer film on the electrodes during electropolymerization and remove any polymer residue via dissolution. The resultant associated polymer formed during electropolymerization are not thermoset but rather thermoplastic. Thermoplastic polymers are susceptible to chemical solvation by an appropriate solvent. For example, polyaniline dissolves in dimethylformamide but not acetonitrile. An appropriate non-aqueous solvent can facilitate continuous or near-continuous/periodic conductivity testing by preventing the formation of polymer film on the electrodes or in the conductivity sensor generally.

An embodiment of the hydrocarbon testing solution includes the non-aqueous solvent that solubilizes or suspends non-solubilized materials in the hydrocarbon fluid. Certain types of heavy crude oils contain asphaltenes that may not adequately solubilize except in combination with long-chain paraffins provided by the non-aqueous solvent.

Useful examples of non-aqueous solvents for use as part of the hydrocarbon testing solution include dimethylformamide; 2, 5-dimethoxytetrahydrofuran; tetrahydrofuran; nitrobenzene; acetonitrile; dimethyl sulfoxide; tributyl phosphate; trimethyl phosphate; propylene carbonate; nitromethane; chlorobenzene; anisole; γ-butyrolactone; methanol; ethanol; propanol and dichloromethane. One of ordinary skill in the art understands that suitable non-aqueous solvents also include other non-aqueous solvents not identified but suitable for electrochemical polymerization processes in the hydrocarbon testing solution.

Conductivity Sensor

The conductivity sensor is an electrolysis chemical cell useful for determining part-per-million/part-per-billion/part-per-trillion (ppm/ppb/ppt) concentrations of the salt in the hydrocarbon testing solution. The conductivity sensor detects electrical current (in amperes; usually microamperes) that results from application of electrical potential (in volts; usually millivolts) through the hydrocarbon testing solution contained in the conductivity sensor. The hydrocarbon testing solution contains an unknown amount of salt. The peak current detected by the conductivity sensor is associated with the polymerization of the electropolymerizable monomer. The height of the peak current correlates to the amount of salt present in the hydrocarbon testing solution, which comes from the hydrocarbon fluid.

The conductivity sensor has a shell or housing that defines an internal void space where conductivity testing occurs. The housing is operable to permit electrical and signal communication between the electrodes and exterior electronic devices, including a potentiostat-galvanostat or a computer controller. Electrical insulation of the external junctions to the electrodes fixes the position of each electrode while also insulating each electrode electrically and fluidly. Such insulation prevents both the hydrocarbon testing fluid and electrical current leakage from the interior to the exterior and between the electrodes on the outside of the conductivity sensor.

The housing is operable to contain the hydrocarbon testing solution. The housing permits the introduction of the hydrocarbon testing solution into and the passing of the exhausted hydrocarbon testing solution from the interior of the conductivity sensor. An embodiment of the conductivity sensor has a housing that is operable to permit the separate and simultaneous introduction of the hydrocarbon fluid, the non-aqueous solvent and the electropolymerizable monomer into the conductivity sensor. In such an embodiment, the hydrocarbon testing solution forms within the housing. An embodiment of the conductivity sensor has a housing that is operable to permit the introduction of the pre-mixed hydrocarbon testing solution.

Some housing configurations on the interior of the conductivity sensor include internal structures and attachments to direct or deflect incoming fluid flow, which may also support mixing in the interior of the sensor. Such configurations include flow deflectors and mixing baffles. Internal structures configurations can prevent introduced fluid flow from directly interfering with conductivity testing by diverting the flow away from the electrodes. Internal structures can also include porous plates and mesh screens at the egress port for the exhausted hydrocarbon testing solution. Such plates and screens remove formed solids, especially polymer strands, from the exhausted hydrocarbon testing solution before it passes from the conductivity sensor.

The conductivity sensor housing is made of an electrically insulated or inert material. The conductivity sensor housing also resists solvation, dissolution and "swelling effects" through prolonged contact with the hydrocarbon fluid as well as the non-aqueous solvent. Examples of useful materials include translucent and opaque thermoset plastics, glass and ceramics. Translucent materials are useful in that it permits visual examination of the conductivity sensor to determine if fouling, damage or a malfunction is occurring. Translucent materials also potentially allow other sensors or detectors to operate simultaneously with the conductivity sensor, including sensors using radiation or a light-based beam detection. Configurations of the sensor housing can also include a secondary, external cladding of metal, polymer or insulation to help resist against exterior physical impact and electrical conduction.

The conductivity sensor includes an electrochemical cell three-electrode set positioned within the housing that is operable to apply the potential to and detect current through the hydrocarbon testing solution. The three electrodes in the three-electrode set are the working electrode, the counter electrode and the reference electrode. The relative position of the three electrodes to one another is not important as long as their position remains consistent and the electrodes are not touching one another. The working and reference electrodes together are operable to induce a potential in the hydrocarbon testing solution. The working and counter electrodes together are operable to detect a current in the hydrocarbon testing solution.

The working electrode is made of glassy carbon, platinum, palladium, gold, carbon-graphite, stainless steel, indium-tin-oxide (ITO) conducting glass, chromium, nickel, copper, silver, lead, zinc or any other service material suitable for electropolymerization in the hydrocarbon testing solution. Platinum is a useful material due to its high chemical stability and that it does not corrode easily. The working electrode has a predefined surface area for determining current density (units current/units area) and interpreting voltammetric results. Various known geometric forms include plate, disk, rectangle, rod and square shapes. Shapes having a well-defined flat surface are preferable to make corrosion detection (that is, surface pitting) and polymer film removal easier.

The material of construction of the working electrode accounts for the type of electropolymerizable monomer in use. For example, those of ordinary skill in the art understand that certain electrode materials are not appropriate for use with thiophene and its derivatives because the electrode material can react with ionic species present in the hydrocarbon testing solution before reaching the electropolymerization potential for thiophene. Examples of inappropriate materials for use with thiophene include copper, lead, silver and zinc-based electrode materials.

The counter electrode is made of platinum or any other service material suitable for electropolymerization in the hydrocarbon testing solution. Various known geometric forms include plate, disk, rectangle, rod, square, mesh and wire shapes. The counter electrode has a predefined surface area for determining current density (units current/units area). The surface area of the counter electrode is larger than the working electrode.

The reference electrode is made of silver/silver chloride; silver/silver nitrate; platinum; standard, reversible or normal hydrogen; saturated calomel (SC); quasi-reference electrode (QRE) or any other known reference material or structure suitable for hydrocarbon and non-aqueous solvent service.

The material of construction for the reference electrode accounts for the type of non-aqueous solvent in use in the hydrocarbon testing solution. For example, those of ordinary skill in the art understand that certain electrode materials are not appropriate for use with acetonitrile because the reference electrode system can begin to suffer from voltage drift after prolonged use. An example of an inappropriate material for use with acetonitrile includes a platinum reference electrode.

The conductivity sensor includes a mixing apparatus positioned within the housing. The mixing apparatus is operable to maintain the intimate nature of the hydrocarbon testing solution. In an embodiment of the conductivity sensor, the mixing apparatus is operable to facilitate fluid motion that passes the exhausted hydrocarbon testing solution and any resultant solids (that is, polymers) from the conductivity sensor. Continuous mixing of the hydrocarbon testing solution permits reliable periodic and continuous conductivity testing.

An embodiment of the mixing apparatus is a mixing blade or impeller that couples to an external drive mechanism and passes through the housing of the conductivity sensor. An embodiment of the mixing apparatus is a magnetic stirring bar that magnetically couples to an external magnetic stirring plate or other drive mechanism. One of ordinary skill in the art can device appropriate means for inducing an appropriate level of fluid circulation in the conductivity sensor to support mixing while not hindering reliable and accurate conductivity testing.

The conductivity sensor can be any size. The scale of the conductivity sensor can range from a device that can fit on a laboratory bench to a version only requiring a few milliliters of the non-aqueous solvent and the hydrocarbon fluid to detect the conductivity of the hydrocarbon testing solution. A smaller sized conductivity sensor reduces the consumption of non-aqueous solvent and electropolymerizable monomer, and produces a smaller amount of exhausted hydrocarbon testing solution for return to the process or disposal. The reduced size also minimizes the amount of precious metal use. The smaller size of electrodes and the conductivity sensor housing, in turn, create and retain a smaller amount of resultant associated polymer.

The conductivity sensor can support conductivity detection using hydrocarbon testing solution as a batch, periodic and continuous manner. The conductivity sensor supports manual, fully automated and combination testing processes.

An embodiment of the conductivity sensor includes a means for removing associated polymer from the interior of the conductivity sensor. In some instances, the resulting associated polymer can accumulate on the interior of the conductivity sensor, including the surfaces of the electrodes. A thickening of resultant conductive polymer film on the working or counter electrode, or both, can cause an increase in the peak current height or a shift to a different voltage value where the peak current occurs. With a conductive polymer, electron transfer from the electrodes to the conductive polymer film conveys the electrons to the outermost layer of the polymer film. A conductivity sensor with electrodes coated in conductive polymer (given all other conditions are steady state) can produce increasing peak current values due to electropolymerizable monomer adding to the conductive polymer film at the polymerization potential of the monomer. The increasing peak current values do not reflect increasing salt concentrations in the hydrocarbon fluids; rather, they reflect improved conductivity through a layer of solid conductive polymeric film. The opposite effect—where insulation occurs and the peak current values become successively reduced—can occur with non-conductive polymer films that are electrochemically polymerizable. In addition, heavy oligomers and polymer strands can attach to and aggregate in areas of the conductivity sensor where fluid flow is static, forming a solid material that hinders fluid flow.

Besides providing continuous mixing of the hydrocarbon testing solution or using the non-aqueous solvent that is also a solvent for the resultant associated polymer, a means for removing polymer from the conductivity sensor interior includes mechanical separation or scraping devices. Mechanical separation devices physically cause the removal of resultant polymer film from surfaces, including the electrodes. Mechanical separation devices include silicone paddles that are resistant to the solvation effects of the non-aqueous solvent and the alkane-dominated hydrocarbon fluid. Such silicone paddles are pliable to not cause distortion to the surface of the electrodes or change their relative position if in direct contact.

Other means include introduction of a solvent directly to the surface of the residual polymer. The residual polymer solvent can be one of the non-aqueous solvent previously described. An embodiment of the conductivity sensor includes a nozzle or port that is operable to introduce a non-aqueous solvent of the resultant associated polymer into the conductivity sensor. A further embodiment of the conductivity sensor includes where the non-aqueous solvent introducing nozzle is operable to direct the non-aqueous solvent onto the three-electrode set. Non-aqueous solvent can be directed onto the electrodes during or in between periods of conductivity testing. An embodiment of the conductivity sensor includes a nozzle or port that is operable for external manipulation. Such a nozzle can direct the non-aqueous solvent onto the electrode set.

Potentiostat-Galvanostat Device

Electrodes of the conductivity sensor are in electrical and signal communication with the potentiostat-galvanostat device. The potentiostat-galvanostat device is operable to induce a potential (in volts) between the working and reference electrodes of the conductivity sensor and to correlate the detected current (in amperes) between the working and counter electrodes. The combination potentiostat-galvanostat device permits the determination of current values, including the "peak" current value, at applied potentials for the hydrocarbon testing solution using the three-electrode conductivity sensor. The use of the three-electrode conductivity sensor in conjunction with the potentiostat-galvanostat device permits controlled application of potential to the hydrocarbon testing solution and correlation and association of the detected current.

Useful potentiostat-galvanostat devices and other voltage-inducing devices are operable to apply a singular potential value across the electrochemical cell, sweeping potential values, where the potential changes between a first value and a second value at a fixed linear "sweep" rate, and cyclical potential values, where the potential changes at the linear sweep rate and repeatedly cycles between the first potential value and the second potential value. An embodiment of the method includes inducing potential in the hydrocarbon testing fluid at a linear sweep rate in a range of from about 5 millivolts (mV/sec) to about 0.5 volts per second. An embodiment of the method includes inducing potential a linear sweep rate of about 20 mV/sec. An embodiment of the method includes inducing potential where the first potential value is about −0.3 V and the second potential value is about +2.5 V with respect to the reference electrode. The potentiostat-galvanostat is operable to associate current values detected by the conductivity sensor to the applied potential values.

Potentiostat-galvanostat devices that include an incorporated monitor or printer, or electronic connections that permit signal communications with external output devices, including monitors, plotters and printers, can directly convey the numerical dataset or a X-Y graphical representation (that is, a voltammogram) of the potential values versus the associated detected current values for direct human interpretation.

The potentiostat-galvanostat device includes those devices that can transfer the potential-current dataset containing the induced range of potential values and the associated range of detected current values using a signal communications pathway to a computer that is operable to interpret the potentiostat-galvanostat data for additional computer-based determinations and system control.

Method for Determining Salt Concentration in the Hydrocarbon Fluid

The method for determining the salt concentration of the hydrocarbon fluid includes the step of forming the hydrocarbon testing solution. The hydrocarbon testing solution comprises hydrocarbon fluid, an electropolymerizable monomer and a non-aqueous solvent. The electropolymerizable monomer is operable in the hydrocarbon testing solution to form a resultant associated polymer at the peak potential of the electropolymerizable polymer.

The method includes the step of introducing the hydrocarbon testing solution into the conductivity sensor. The hydrocarbon testing solution is a mixture of the hydrocarbon fluid, the electropolymerizable monomer and the non-aqueous solvent. The hydrocarbon fluid contains an amount of salt. The conductivity sensor is a three-electrode electrochemical cell having a working, counter and reference electrodes.

The method includes the step of inducing a range of potential across the hydrocarbon testing solution contained in the conductivity sensor. The range of induced potential includes the peak potential of the electropolymerizable polymer. The working and reference electrodes induce the range of potential through the hydrocarbon testing solution. The inducement causes at least a portion of the electropolymerizable monomer in the hydrocarbon testing solution polymerizes into the resultant associated polymer. The inducement also causes the hydrocarbon testing solution to form an exhausted hydrocarbon testing solution. During electropolymerization, the conductivity sensor detects the peak current between the working and counter electrodes.

The method includes the step of detecting a range of electrical current associated with the range of potential induced using the conductivity sensor, where the range of detected electrical current includes the peak current. When performing sweeping or cyclic voltammetry, the detected current increases as the potential approaches the polymerization potential of the monomer. Upon achieving the polymerization potential, the detected current value "peaks" as electron-transfer occurs through the radicalized monomer units (supported by the salt in the hydrocarbon testing solution) and the resultant associated polymer forms. After surpassing the polymerization potential, the detectable current declines with changing potential values, including increasing potential. Although not intending to be bound by theory, it is believed that the drop-off in detected current reflects the depletion of electropolymerizable monomer proximate to the working and counter electrodes.

Using either manual or automated analysis techniques, the peak current height value is determined. One of ordinary skill in the art of electrochemistry is capable of determining the peak current height value from the results of sweeping or cyclic voltammetry. Automated analysis techniques can include using a computer that is operable to automatically receive and process potential-current data from the potentiostat-galvanostat using a set of computer-readable instruction (that is, program) and data stored in a combination of physical and virtual computer-accessible memory. The peak current height value is an absolute value based upon the composition of the hydrocarbon testing solution, which includes the amount of salt. Process-related factors, including fluid temperature, do not affect the determined salt concentration values.

The method includes the step of determining the salt concentration of the hydrocarbon fluid using the range of potential induced across the hydrocarbon testing solution and the range of electrical current detected by the conductivity sensor. Given steady-state concentration conditions for the hydrocarbon testing solution, the salt concentration in the hydrocarbon testing solution is determinable via correlation to the peak current height value. The operator can use manual analysis techniques, including comparison to prior conductivity testing results, standard peak current height value/salt concentration charts for the hydrocarbon testing solution or process trend analysis to determine the salt concentration of the hydrocarbon testing solution. The operator can also use automated computational devices, including a computer with a program designed for analyzing the peak current height value and the sweeping or cyclic voltammetry data to determine the salt concentration of the hydrocarbon testing solution. The operator can determine the salt concentration in the hydrocarbon fluid using the salt concentration value for the hydrocarbon testing solution knowing the proportional amount of hydrocarbon fluid in the hydrocarbon testing solution.

An embodiment of the method includes the step of passing the passing the exhausted hydrocarbon testing solution from the conductivity sensor. The process can pass exhausted hydrocarbon testing solution to the system from which the hydrocarbon fluid with salt was drawn from or it can be disposed of through a separate facility or system, including a facility that is operable to recycle unused recyclable monomer, the non-aqueous solvent, or both.

An embodiment of the process includes the step of introducing a non-aqueous solvent of the resultant associated polymer into the conductivity sensor. The non-aqueous solvent introduced is operable to dissolve the resultant associated polymer from the conductivity sensor and help maintain the sensor is operating condition. In an embodiment of the method, the non-aqueous solvent of the resultant associated polymer is introduced into the conductivity sensor such that the exhausted hydrocarbon testing solution present in the conductivity sensor passes from the conductivity sensor.

Method for Salt Extraction from Hydrocarbon Fluid

A method for extracting salt from the hydrocarbon fluid includes the step of performing the method for determining the salt concentration of the hydrocarbon fluid using the conductivity sensor and the hydrocarbon testing solution as previously described. A salt-extraction fluid is used to remove at least some of the salt from the hydrocarbon fluid. Separating the treated hydrocarbon fluid from the salt-extraction fluid effectively desalinates the hydrocarbon fluid. Traditional desalination techniques easily separate the salt-extraction fluid from the salt for reuse and recycle.

The method includes the step of introducing an amount of salt-extracting fluid into the hydrocarbon fluid. The salt-extracting fluid and the hydrocarbon fluid intermingle. The salt-bearing salt-extracting fluid and the desalinated hydrocarbon fluid form from the treatment. Introduction of an appropriate amount of salt-extracting fluid is a function of the concentration of the salt in the hydrocarbon fluid.

Determining the amount of the hydrocarbon fluid to be treated is also an important factor in determining the appropriate amount of salt-extracting fluid to introduce. The amount of hydrocarbon fluid can be fixed, as in the amount in a tank or vessel, or can be continuous, as in a continuous flow of material. Determining the fixed or flow rate of the hydrocarbon fluid using traditional process engineering or mathematical techniques provides a reliable estimate of the amount of salt that can be extracted from the hydrocarbon fluid using the treatment fluid. One of ordinary skill understands that several relationships, including process configurations and economics, influence the determination of the amount of salt-extraction fluid to apply to the hydrocarbon fluid and the level of salt extraction from the hydrocarbon fluid to achieve.

An embodiment of the method includes introducing additional chemicals with the salt-extracting fluid. Useful additional chemicals include emulsifiers, detergents and surfactants, to improve the contact between the salt-extraction fluid and the hydrocarbon fluid to improve the removal of the salt from the hydrocarbon fluid.

A useful salt-extraction fluid is water. Introducing water as the salt-extraction fluid into the hydrocarbon fluid can occur as a liquid, a steam or as a dual-phase fluid. The vaporous form can be wet, dry or superheated steam. The pressure of the steam can be in a range of from about 15 to about 1000 pounds per square inch gauge (psig). The temperature of the steam can be in a range of from about 105° C. to about 280° C. Water provided in liquid form can be in a temperature range of from about 1° C. to about 99° C.

The method includes separating the salt-bearing salt-extracting fluid from the desalinated hydrocarbon fluid. Separating the salt-bearing salt-extracting fluid from the desalinated hydrocarbon fluid occurs downstream from the salt-extraction fluid introduction point. The resultant is a desalinated hydrocarbon fluid ready for transport, petroleum refining and petrochemical processing. Those of skill in the art know such means and processes for removing salt from the salt-extracting fluid.

An embodiment of the method includes introducing a fluid into the hydrocarbon fluid that neutralizes or eliminates a specific salt or ionic specie. For example, the salt-extraction process can include introduction of a fluid that preferentially reacts with a particular salt (sodium chloride) or a certain halide type (chloride ions). Such a technique may remove a dominant specie of salt or ion and permit less expensive or intrusive process to remove other salts or ions before further processing.

Supporting Equipment

Embodiments include many additional standard components or equipment that enables and makes operable the described apparatus, process, method and system. Examples of such standard equipment known to one of ordinary skill in the art includes heat exchanges, pumps, blowers, reboilers, steam generation, condensate handling, membranes, single and multi-stage compressors, separation and fractionation equipment, valves, switches, controllers and pressure-, temperature-, level- and flow-sensing devices.

Operation, control and performance of portions of or entire steps of a process or method can occur through human interaction, pre-programmed computer control and response systems, or combinations thereof.

What is claimed is:

1. A system for determining a salt concentration of a hydrocarbon fluid using a conductivity sensor and a hydrocarbon testing solution, comprising:
   a sampling line coupled to a hydrocarbon fluid supply line and configured to divert a portion of hydrocarbon fluid from the hydrocarbon fluid supply line;
   a solvent injection line coupled to the sampling line and configured to introduce a non-aqueous solvent into the sampling line to mix with the portion of hydrocarbon fluid;
   a monomer injection line coupled to the sampling line and configured to introduce an electropolymerizable monomer into the sampling line to mix with the portion of hydrocarbon fluid and the non-aqueous solvent to from a hydrocarbon testing solution
   a conductivity sensor coupled to the sample line, wherein the sample line is further configured to introduce the hydrocarbon testing solution to the interior of the conductivity sensor, the conductivity sensor comprising a working electrode, a counter electrode and a reference electrode; and
   a computer controller comprising computer-accessible memory, the computer-accessible memory having computer-readable instructions stored thereon that, when executed, cause the computer controller to:
      induce a sweeping potential in the hydrocarbon testing solution between a first pre-set potential value and a pre-set second potential value using the working electrode and the reference electrode, such that at least a portion of the electropolymerizable monomer in the hydrocarbon testing solution polymerizes into a resultant associated polymer; and
      determine the concentration of salt in the hydrocarbon fluid in the hydrocarbon fluid supply line.

2. The system of claim 1, comprising:
   a polymer solvent line coupled to the conductivity sensor and configured to introduce a polymer solvent into the conductivity sensor; and
   a polymer solvent flow control valve coupled to the polymer solvent line and in signal communication with the computer controller.

3. The system of claim 2, the computer-accessible memory having computer-readable instructions stored thereon that, when executed, cause the computer controller to:
   periodically introduce an amount of polymer solvent into the conductivity sensor by transmitting a signal to the polymer solvent flow control valve, the amount of polymer solvent sufficient to remove the resultant associated polymer from the conductivity sensor.

4. The system of claim 1, comprising a sampling return line coupled to the conductivity sensor and configured to convey exhausted hydrocarbon testing solution from the conductivity sensor to the hydrocarbon fluid supply line.

5. The system of claim 1, comprising a display monitor, the computer-accessible memory having computer-readable instructions stored thereon that, when executed, cause the computer controller to provide computer-processed information of conductivity testing on the display monitor.

6. The system of claim 1, comprising a hydrocarbon fluid flow sensor configured to detect a rate of fluid flow through the hydrocarbon fluid supply line, wherein the hydrocarbon fluid flow sensor is in signal communication with the computer controller.

7. The system of claim 6, comprising:
a steam injection line coupled to the hydrocarbon fluid supply line and configured to introduce steam into the hydrocarbon fluid supply line to mix with the hydrocarbon fluid;
a steam flow control valve coupled to the steam injection line and in signal communication with the computer controller; and
a steam flow sensor configured to provide a signal in response to the detected rate of steam flow through the steam injection line, wherein the steam flow sensor is in signal communication with the computer controller;
a steam pressure sensor configured to provide a signal in response to the pressure of the steam in the steam injection line, wherein the steam pressure sensor is in signal communication with the computer controller; and
a steam temperature sensor configured to provide a signal in response to the temperature of the steam in the steam injection line, wherein the steam pressure sensor is in signal communication with the computer controller.

8. The system of claim 7, the computer-accessible memory having computer-readable instructions stored thereon that, when executed, cause the computer controller to:
determine an amount of steam to introduce to the hydrocarbon fluid in the hydrocarbon fluid supply line to for downstream salt extraction, the determination based on a flow signal from the hydrocarbon fluid flow sensor, a flow signal from the steam flow sensor, a pressure signal from the steam pressure sensor and a temperature signal from the steam temperature sensor.

9. The system of claim 1, comprising:
a sampling line flow control valve coupled to the sampling line and in signal communication with the computer controller; and
a sampling line flow sensor configured to provide a signal in response to the detected rate of fluid flow through the sampling line, wherein the sampling line flow sensor is in signal communication with the computer controller.

10. The system of claim 1, comprising:
a solvent injection line flow control valve coupled to the solvent injection line and in signal communication with the computer controller; and
a solvent injection line flow sensor configured to provide a signal in response to the detected rate of fluid flow through the solvent injection line, wherein the solvent injection line sensor is in signal communication with the computer controller.

11. The system of claim 1, comprising:
a monomer injection line flow control valve coupled to the monomer injection line and in signal communication with the computer controller; and
a monomer injection line flow sensor configured to provide a signal in response to the detected rate of fluid flow through the monomer injection line, wherein the monomer injection line flow sensor is in signal communication with the computer controller.

12. The system of claim 1, the computer-accessible memory having computer-readable instructions stored thereon that, when executed, cause the computer controller to:
detect a range of electrical current associated with the range of sweeping potential induced using the working electrode and the counter electrode.

13. The system of claim 12, wherein determine the concentration of salt in the hydrocarbon fluid in the hydrocarbon fluid supply line comprises determine the salt concentration of the hydrocarbon fluid using the range of sweeping potential induced across the hydrocarbon testing solution and the range of electrical current detected by the conductivity sensor.

14. The system of claim 1, wherein the range of sweeping potential includes the peak potential of the resultant polymer.

15. The system of claim 1, wherein the sweeping potential is induced at a linear sweep rate in a range of about 5 millivolts per second (mV/sec) to about 0.5 volts per second.

16. The system of claim 1, wherein the electropolymerizable monomer is selected from the group consisting of thiophene, thiophene-derivatives, aniline, aniline-derivatives, crown ethers and combinations thereof.

17. The system of claim 1, wherein the conductivity sensor comprises a mixing apparatus, the computer-accessible memory having computer-readable instructions stored thereon that, when executed, cause the computer controller to transmit a signal to the mixing apparatus to provide continuous stirring of the hydrocarbon testing solution.

18. The system of claim 1, wherein the working electrode has a first surface area and the counter electrode has a second surface area, wherein the second surface area is greater than the first surface area.

* * * * *